US011389514B2

(12) United States Patent
Allen

(10) Patent No.: US 11,389,514 B2
(45) Date of Patent: Jul. 19, 2022

(54) MYELOPEROXIDASE COMPOSITIONS AND METHODS FOR INHIBITION OF LIPOPOLYSACCHARIDES AND LIPID A

(71) Applicant: EXOXEMIS, INC., Little Rock, AR (US)

(72) Inventor: Robert C. Allen, Omaha, NE (US)

(73) Assignee: EXOXEMIS, INC., Little Rock, AR (US)

(*) Notice: Subject to any disclaimer, the term of this patent is extended or adjusted under 35 U.S.C. 154(b) by 0 days.

(21) Appl. No.: 16/302,449

(22) PCT Filed: Apr. 13, 2017

(86) PCT No.: PCT/US2017/027458
§ 371 (c)(1),
(2) Date: Nov. 16, 2018

(87) PCT Pub. No.: WO2017/204918
PCT Pub. Date: Nov. 30, 2017

(65) Prior Publication Data
US 2019/0183983 A1    Jun. 20, 2019

Related U.S. Application Data

(60) Provisional application No. 62/342,382, filed on May 27, 2016.

(51) Int. Cl.
| | |
|---|---|
| *A61K 38/44* | (2006.01) |
| *A61K 33/00* | (2006.01) |
| *A61P 31/04* | (2006.01) |
| *A61K 9/00* | (2006.01) |
| *A61K 31/401* | (2006.01) |
| *A61K 31/198* | (2006.01) |

(52) U.S. Cl.
CPC ............ *A61K 38/44* (2013.01); *A61K 9/0014* (2013.01); *A61K 31/198* (2013.01); *A61K 31/401* (2013.01); *A61K 33/00* (2013.01); *A61P 31/04* (2018.01); *C12Y 111/01007* (2013.01); *C12Y 111/02002* (2013.01)

(58) Field of Classification Search
None
See application file for complete search history.

(56) References Cited

U.S. PATENT DOCUMENTS

| | | | |
|---|---|---|---|
| 5,089,274 A | 2/1992 | Marra et al. | |
| 5,389,369 A * | 2/1995 | Allen | C12Y 111/01007 424/94.4 |
| 5,451,402 A * | 9/1995 | Allen | A61L 2/22 424/94.4 |
| 5,565,197 A * | 10/1996 | Allen | A01N 63/00 424/94.1 |
| 5,731,008 A * | 3/1998 | Morrow | A61P 31/22 424/613 |
| 5,888,505 A | 3/1999 | Allen | |
| 6,294,168 B1 | 9/2001 | Allen | |
| 2009/0280102 A1 | 12/2009 | Becquerelle et al. | |
| 2014/0120076 A1 * | 5/2014 | Stephens, Jr. | A61K 31/327 424/94.4 |

FOREIGN PATENT DOCUMENTS

| | | |
|---|---|---|
| GB | 2108387 | 5/1983 |
| WO | 2009137697 A1 | 11/2009 |
| WO | 2013009910 | 1/2013 |

OTHER PUBLICATIONS

Allen'2011, Myeloperoxidase selectively binds and selectively kills microbes, Infection and Immunity, Jan. 2011, p. 474-485 (Year: 2011).*
Raetz et al., Lipopolysaccharide Endotoxins, Annu. Rev. Biochem., 2002, 71:635-700 (Year: 2002).*
Reber et al. "Neutrophil myeloperoxidase diminishes the toxic effects and mortality induced by lipopolysaccharide" J. Exp. Med., 2017, vol. 214, No. 5, pp. 1249-1258.
Clark J et al: "Efficacy of E-101 Solution, a Myeloperoxidase Based Antimicrobial, in Different Rat Localized Wound Infection Models", Database accession No. PREV200900235747.
Biosciences Information Service, Philadelphia, PA, US; 2008, Becquerelle S et al: "E-101 Solution Effectively Reduces Pseudomonas aeruginosa in a Rat Heat Induced Necrosis Model", Database accession No. PREV2009002357 48.
Denys G et al: "In Vitro Characterization of E-101 Solution, a Novel Myeloperoxidase-Based Antimicrobial Agent", Database accession No. PREV200900235062.
Supplemental European Search report for Appl No. EP 17 80 3212 dated Nov. 28, 2019.
Annex to the European Search Report on European Patent Application No. EP 17 80 3212.
Extended European Search report for 17803212.4 dated Dec. 16, 2019.
Information on Search Strategy for EP 17 80 3212.
Certificate of Correction for U.S. Pat. No. 5,888,505 dated Mar. 30, 1999.
Npl-copyright-statement.
Watanabe; Translation of Office Action from related Japanese Application 2020-077140; dated May 24, 2021; 5 Pgs.
Savenkova et al.; Tyrosyl Radical Generated by Myeloperoxidase Is a Physiological Catalyst for the Initiation of Lipid Peroxidation in Low Density Lipoprotein; The Journal of Biological Chemistry; Aug. 12, 1994; pp. 20394-20400; vol. 269; No. 32.
Denys et al.; In vitro antibacterial activity of E-101 Solution, a novel myeloperoxidase-mediated antimicrobial, against Gram-positive and Gram-negative pathogens; Journal of Antimicrobial Chemotherapy; Nov. 30, 2010; pp. 335-342; vol. 66.

* cited by examiner

*Primary Examiner* — Louise W Humphrey
*Assistant Examiner* — Srikanth Patury
(74) *Attorney, Agent, or Firm* — K&L Gates LLP

(57) ABSTRACT

Compositions comprising a combination of myeloperoxidase and a peroxide-producing oxidase and methods of using the compositions to inactivate gram negative bacterial lipopolysaccharides and lipid A endotoxin are provided.

6 Claims, No Drawings

MYELOPEROXIDASE COMPOSITIONS AND METHODS FOR INHIBITION OF LIPOPOLYSACCHARIDES AND LIPID A

CROSS REFERENCE TO RELATED APPLICATIONS

The present application is a National Stage of International Application No. PCT/US2017/027458, filed on Apr. 13, 2017, claims the benefit of U.S. Provisional Application No. 62/342,382, filed May 27, 2016, the entire contents of which are being incorporated herein by reference.

BACKGROUND

Bacterial toxins promote infection and disease by directly damaging host tissues and by disabling the immune system. There are two types of bacterial toxins: exotoxins and endotoxins. Exotoxins are secreted by bacteria and cause a variety of symptoms, depending on the bacteria. For example, bacterial exotoxins are responsible for diphtheria, tetanus, botulism, cholera, diarrhea, scarlet fever, toxic shock syndrome, and meningitis. Endotoxins are lipopolysaccharides ("LPS"), and the universal toxic lipid component of the lipopolysaccharide molecule is lipid A. Endotoxins are an integral part of the cell wall of gram-negative bacteria and are liberated on cell death. The presence of endotoxins in the blood can produce fever, diarrhea, septic shock, and loss of function of internal organs such as kidneys, liver, adrenal glands, and lungs.

Gram-negative bacterial infections are challenging to treat because the killing of the bacteria leads to the release of endotoxins. For example, the Jarisch-Herxheimer reaction, a condition with signs and symptoms resembling bacterial sepsis, occurs when endotoxin is released from gram-negative spirochete bacteria, such as *Treponema* (causative agent of syphilis) and *Borellia* (causative agent of Lyme's disease) during antibiotic treatment. Therefore, there is a need for a microbicidal agent against gram-negative bacteria that will not only kill the bacteria but also inactivate the endotoxin released on death of the bacteria. As further discussed below, the present disclosure addresses this and other needs.

It is known in the art that a myeloperoxidase/hydrogen peroxide/halide system kills bacterial infectious agents, including gram-negative bacteria. As disclosed in U.S. Pat. Nos. 5,888,505, 6,294,168, and 8,945,540, when the concentration is limiting, myeloperoxidase selectively binds to and, in the presence of peroxide and halide, kills target microorganisms without significantly damaging other components of the medium, such as host cells and normal flora. Due to the selective binding properties of myeloperoxidase, when a target microorganism, such as a pathogenic microorganism, has a binding capacity for myeloperoxidase greater than that of a desired microorganism, such as members of the lactic acid bacteria of the normal flora, the target microorganism selectively binds the myeloperoxidase with little or no binding of the myeloperoxidase by the desired microbes. In this regard, myeloperoxidase demonstrates a high degree of selective binding and selective killing of all gram-negative bacteria tested.

Target bound myeloperoxidase, in the presence of peroxide and halide, catalyzes halide oxidation and facilitates the disproportionation of peroxide to singlet molecular oxygen ($^1O_2$) at the surface of the target microorganism. Singlet molecular oxygen has a microsecond lifetime and a reactive radius of about 0.2 micrometer. As such, combustive microbicidal action is limited to myeloperoxidase-bound microbes with a minimum of collateral damage to desired microbes or host cells. Thus, as disclosed in U.S. Pat. Nos. 5,888,505, 6,294,168, and 8,945,540, myeloperoxidase can be employed as an antiseptic in the therapeutic or prophylactic treatment of human or animal subjects to selectively bind to and kill pathogenic microorganisms with a minimum of collateral damage to host cells and normal flora of the host.

It is also known in the art that a myeloperoxidase/hydrogen peroxide/halide system is effective in detoxifying exotoxins. See, e.g., Agner, K., (1950), "Studies On Peroxidative Detoxification of Purified Diptheria Toxin", JEM, 92 (4) 337-347; Agner, K., (1955), "Peroxidative Detoxification of Diptheria Toxin Studied by Using 1131, Recueil", 74:373-376; Agner, K., (1947), "Detoxicating Effect of Verdoperoxidase on Toxins", Nat. 4034:271-272 (tetanus toxin); and Ool et al. (1994), "Inactivation of Clostridium difficile Cytotoxin by the Neutrophil Myeloperoxidase System", J. Infect. Dis. 149(2):215-219.

All of the foregoing references teach that hydrogen peroxide is necessary for antitoxin activity. The prior art does not teach or remotely suggest that myeloperoxidase alone, in the absence of haloperoxidase activity, is effective in detoxifying endotoxins.

The inventor of the present disclosure has discovered that myeloperoxidase not only binds to gram-negative bacteria, but also binds to gram-negative bacteria endotoxins (lipopolysaccharide) and to lipid A (the component of endotoxin responsible for toxicity), and that such binding inhibits the toxic activity of lipopolysaccharide and lipid A. Moreover, the inventor of the present disclosure has surprisingly discovered that myeloperoxidase inhibition of endotoxin lipopolysaccharide/lipid A does not require haloperoxidase enzymatic generation of hypochlorite or singlet molecular oxygen. Nothing in the prior art discloses that myeloperoxidase would be effective as an anti-lipopolysaccharide (anti-endotoxin) and anti-lipid A agent in the absence of haloperoxidase activity.

The present disclosure demonstrates that myeloperoxidase compositions used to treat bacterial infections have the additional advantage of inhibiting (detoxifying) the lipopolysaccharide and lipid A endotoxin activity of gram-negative bacterial pathogens. The present disclosure thus meets a need to provide an effective treatment for gram-negative bacterial infections that both kills the bacteria and inhibits the endotoxins released on death of the bacteria.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure relates to methods for the treatment of gram-negative microbial infections using compositions comprising myeloperoxidase to bind to and inactivate lipopolysaccharide (endotoxin) and lipid A, the lipid component of endotoxin responsible for the toxicity of gram-negative bacteria. The present disclosure provides methods of treating a human or animal subject having a gram-negative bacterial infection comprising administering to the site of the gram-negative bacterial infection in the subject a composition comprising myeloperoxidase, wherein the composition acts to detoxify lipopolysaccharides and lipid A present at the site of the infection.

In some embodiments, the myeloperoxidase composition further comprises a peroxide-producing oxidase. Examples of peroxide-producing oxidases include glucose oxidase, cholesterol oxidase and galactose oxidase. In some embodiments, the peroxide-producing oxidase is glucose oxidase. In some embodiments, the myeloperoxidase/oxidase composition further comprises halide.

In some embodiments, the methods further comprise contacting the site of infection with the myeloperoxidase/oxidase composition in the presence of a substrate for the oxidase. However, the antitoxin activity of the myeloperoxidase is not dependent on the production of hydrogen peroxide.

In some embodiments the myeloperoxidase/oxidase composition further comprises at least two amino acids. In some embodiments, the at least two amino acids are selected from the group consisting of glycine, l-alanine, d-alanine, l-alanine anhydride, l-glutamine, l-glutamic acid, glycine anhydride, hippuric acid, l-histidine, l-leucine, d-leucine, l-isoleucine, d-isoleucine, l-lysine, l-ornithine, d-phenylalanine, l-phenylalanine, l-proline, l-hydroxyproline, l-serine, taurine, l-threonine, d-threonine, l-tyrosine, l-valine, d-valine, beta amino acids, such as beta alanine, l-beta-homoleucine, d-beta-homoleucine, 3-aminobutanoic acid, 1-2,3-diaminopropionic acid monohydrochloride, d-2,3-diaminopropionic acid monohydrochloride, l-3-aminoisobutyric acid, d-3-aminoisobutyric acid, ethyl 3-aminobutyrate, sarcosine methyl ester hydrochloride and nipecotic acid, or an alkyl ester or pharmaceutically acceptable salt thereof.

In other embodiments, the at least two amino acids are selected from the group consisting of glycine, l-alanine, d-alanine, l-alanine anhydride, l-glutamine, l-glutamic acid, glycine anhydride, hippuric acid, l-histidine, l-leucine, d-leucine, l-isoleucine, d-isoleucine, l-lysine, l-ornithine, d-phenylalanine, l-phenylalanine, l-proline, l-hydroxyproline, l-serine, taurine, l-threonine, d-threonine, l-tyrosine, l-valine, and d-valine, or an alkyl ester or pharmaceutically acceptable salt thereof.

In some embodiments the myeloperoxidase/oxidase composition further comprises at least three amino acids. In some embodiments, the at least three amino acids are selected from the group consisting of glycine, l-alanine, d-alanine, l-alanine anhydride, l-glutamine, l-glutamic acid, glycine anhydride, hippuric acid, l-histidine, l-leucine, d-leucine, l-isoleucine, d-isoleucine, l-lysine, l-ornithine, d-phenylalanine, l-phenylalanine, l-proline, l-hydroxyproline, l-serine, taurine, l-threonine, d-threonine, l-tyrosine, l-valine, d-valine, beta amino acids, such as beta alanine, l-beta-homoleucine, d-beta-homoleucine, 3-aminobutanoic acid, 1-2,3-diaminopropionic acid monohydrochloride, d-2,3-diaminopropionic acid monohydrochloride, l-3-aminoisobutyric acid, d-3-aminoisobutyric acid, ethyl 3-aminobutyrate, sarcosine methyl ester hydrochloride and nipecotic acid, or an alkyl ester or pharmaceutically acceptable salt thereof.

In other aspects, the at least three amino acids are selected from the group consisting of glycine, l-alanine, d-alanine, l-alanine anhydride, l-glutamine, l-glutamic acid, glycine anhydride, hippuric acid, l-histidine, l-leucine, d-leucine, l-isoleucine, d-isoleucine, l-lysine, l-ornithine, d-phenylalanine, l-phenylalanine, l-proline, l-hydroxyproline, l-serine, taurine, l-threonine, d-threonine, l-tyrosine, l-valine, and d-valine, or an alkyl ester or pharmaceutically acceptable salt thereof.

In some embodiments, the three amino acids are glycine, alanine, and proline.

In one embodiment, the compositions of the present disclosure comprise from 1 to 50,000 µg/ml of myeloperoxidase. In other embodiments, the compositions of the present disclosure comprise 0.1 to about 500 mM of each of the at least two amino acids. In one representative embodiment, the compositions of the present disclosure comprise from 10 to 5,000 µg/ml of myeloperoxidase, from 0.3 to 50 mM of glycine, from 0.3 to 50 mM of l-alanine, from 0.3 to 50 mM of l-proline, and from 1 to 500 U/ml of glucose oxidase.

In some aspects of the present disclosure, the human or animal subject to be treated is suffering from a gram-negative bacterial infection of the gums, eyes, ears, skin, soft tissue, wounds, vaginal areas, groin areas, bed sores or burn areas. In some embodiments, the infection is a polymicrobial infection. In other embodiments, the infection is caused, at least in part, by a multidrug resistant gram-negative bacteria.

DETAILED DESCRIPTION

The present disclosure is broadly directed to methods of treating a human or animal subject having a gram-negative bacterial infection comprising administering to the site of the gram-negative bacterial infection in the subject a composition comprising myeloperoxidase, wherein the composition acts to detoxify lipopolysaccharides and lipid A present at the site of the infection. Myeloperoxidase compositions are capable of binding to and detoxifying lipopolysaccharide (endotoxin) and lipid A (the purified component of endotoxin responsible for toxicity).

In some embodiments, the myeloperoxidase composition further comprises a peroxide-producing oxidase. In embodiments where the myeloperoxidase composition includes a peroxide-producing oxidase, the myeloperoxidase and peroxide-producing oxidase act synergistically to increase the detoxifying activity of the myeloperoxidase.

The myeloperoxidase/oxidase compositions are effective in detoxifying lipopolysaccharide and lipid A with or without amino acids. In embodiments where amino acids are present, the myeloperoxidase/oxidase composition further comprises at least two amino acids. In some embodiments the myeloperoxidase/oxidase composition further comprises three amino acids. In some embodiments, the myeloperoxidase composition further comprises a halide, e.g. chloride, bromide, or iodide.

In one aspect, the methods of the present disclosure are highly suitable for the topical treatment of susceptible infections in a human or non-human mammalian subject at sites permitting direct contact of the myeloperoxidase compositions of the present disclosure with the microbial infection, such as, for example, gram-negative bacterial infections of the skin, eyes, ears, mouth, nasal and sinus passages, traumatic injury sites, surgical sites and the like. When in contact with host tissue, the myeloperoxidase compositions of the present disclosure can inactivate lipid A and lipopolysaccharides without associated host tissue destruction or disruption of normal flora.

Myeloperoxidase useful in the present disclosure is a halide: hydrogen peroxide oxidoreductase (e.g., EC No. 1.11.1.7 and EC No. 1.11.1.10 under the International Union of Biochemistry) for which halide, i.e., chloride, bromide, or iodide is the electron donor or reductant and peroxide is the electron receiver or oxidant. While haloperoxidase activity is necessary for microbicidal activity, myeloperoxidase inhibits both lipopolysaccharide and lipid A through a direct binding independent of haloperoxidase enzymatic action.

For most purposes, the compositions of the present disclosure will generally comprise at least about 0.05 µg/ml of myeloperoxidase. In some embodiments, the compositions of the present disclosure will comprise from about 1 to about 50,000 µg/ml of myeloperoxidase, more preferably from about 5 to about 10,000 µg/ml of myeloperoxidase, and even more preferably from about 10 to about 5,000 µg/ml of myeloperoxidase.

Peroxide-producing oxidases useful in the present disclosure include, for example, oxidases, such as glucose oxidase, cholesterol oxidase and galactose oxidase. As a representative example, when the oxidase is glucose oxidase and its substrate is glucose, the compositions of the present disclosure may comprise from about 0.05 to about 3,000 U/ml, more preferably from about 0.1 to about 1,000 U/ml, and even more preferably from about 1 to about 500 U/ml of glucose oxidase, and from about 0.1 to about 100 mM, more preferably from about 0.5 to about 80 mM, and even more preferably from about 1 to about 50 mM glucose.

Myeloperoxidase inhibits both lipopolysaccharide and lipid A endotoxin activities through a direct binding independent of haloperoxidase enzymatic action. In the haloperoxidase enzymatic embodiment, the methods further comprise contacting the site of infection with the composition in the presence of halide and a substrate for the oxidase.

In some embodiments, the compositions of the present disclosure comprise at least two amino acids selected from the group consisting of glycine, l-alanine, d-alanine, l-alanine anhydride, l-glutamine, l-glutamic acid, glycine anhydride, hippuric acid, l-histidine, l-leucine, d-leucine, l-isoleucine, d-isoleucine, l-lysine, l-ornithine, d-phenylalanine, l-phenylalanine, l-proline, l-hydroxyproline, l-serine, taurine, l-threonine, d-threonine, l-tyrosine, l-valine, d-valine, beta amino acids, such as beta alanine, l-beta-homoleucine, d-beta-homoleucine, 3-aminobutanoic acid, l-2,3-diaminopropionic acid monohydrochloride, d-2,3-diaminopropionic acid monohydrochloride, l-3-aminoisobutyric acid, d-3-aminoisobutyric acid, and ethyl 3-aminobutyrate, as well as the alkyl esters thereof, such as, for example, l-alanine methyl ester, d-alanine methyl ester, l-lysine methyl ester dihydrochloride, glycine methyl ester hydrochloride, l-proline methyl ester hydrochloride, l-valine ethyl ester hydrochloride and ethyl 2-aminopropanoate, and N-substituted amino acids, such as sarcosine methyl ester hydrochloride and nipecotic acid.

In other embodiments, the compositions of the present disclosure comprise at least two amino acids selected from the group consisting of glycine, l-alanine, d-alanine, l-alanine anhydride, l-glutamine, l-glutamic acid, glycine anhydride, hippuric acid, l-histidine, l-leucine, d-leucine, l-isoleucine, d-isoleucine, l-lysine, l-ornithine, d-phenylalanine, l-phenylalanine, l-proline, l-hydroxyproline, l-serine, taurine, l-threonine, d-threonine, l-tyrosine, l-valine, and d-valine, as well as alkyl esters thereof.

In some embodiments the myeloperoxidase/oxidase composition further comprises at least three amino acids. In some embodiments, the at least three amino acids selected from the group consisting of glycine, l-alanine, d-alanine, l-alanine anhydride, l-glutamine, l-glutamic acid, glycine anhydride, hippuric acid, l-histidine, l-leucine, d-leucine, l-isoleucine, d-isoleucine, l-lysine, l-ornithine, d-phenylalanine, l-phenylalanine, l-proline, l-hydroxyproline, l-serine, taurine, l-threonine, d-threonine, l-tyrosine, l-valine, d-valine, beta amino acids, such as beta alanine, l-beta-homoleucine, d-beta-homoleucine, 3-aminobutanoic acid, l-2,3-diaminopropionic acid monohydrochloride, d-2,3-diaminopropionic acid monohydrochloride, l-3-aminoisobutyric acid, d-3-aminoisobutyric acid, ethyl 3-aminobutyrate, sarcosine methyl ester hydrochloride and nipecotic acid, or an alkyl ester or pharmaceutically acceptable salt thereof.

In other aspects, the at least three amino acids are selected from the group consisting of glycine, l-alanine, d-alanine, l-alanine anhydride, l-glutamine, l-glutamic acid, glycine anhydride, hippuric acid, l-histidine, l-leucine, d-leucine, l-isoleucine, d-isoleucine, l-lysine, l-ornithine, d-phenylalanine, l-phenylalanine, l-proline, l-hydroxyproline, l-serine, taurine, l-threonine, d-threonine, l-tyrosine, l-valine, and d-valine, or an alkyl ester or pharmaceutically acceptable salt thereof.

In some embodiments, the three amino acids are glycine, alanine, and proline.

Useful amounts of the amino acids employed in the compositions of the present disclosure will vary depending on the amount of myeloperoxidase in the compositions and conditions present in the environment of use. For most purposes, the compositions of the present disclosure will generally comprise from about 0.1 to about 500 mM, more preferably from about 0.2 to about 100 mM, and even more preferably from about 0.3 to about 50 mM of each of the amino acids.

Compositions of the present disclosure comprising myeloperoxidase, a peroxide producing oxidase, with or without amino acids, inhibit endotoxins in the absence of substrate, and therefore, in the absence of haloperoxidase enzyme activity. However, the compositions of the present disclosure in combination with a substrate for the peroxide-producing oxidase may produce equivalent or somewhat greater and extended lipopolysaccharide (endotoxin) and lipid A inhibition (i.e., haloperoxidase action) compared to the compositions in the absence of a substrate for the peroxide-producing oxidase.

In embodiments that include a substrate for the peroxide-producing oxidase, the activity of the myeloperoxidase compositions of the present disclosure is microbicidal due to the reaction of peroxide and chloride or bromide to form hypohalite, and the reaction of peroxide and hypohalite to form singlet molecular oxygen. Particularly useful agents for the purpose of producing a peroxide include, for example, oxidases, such as glucose oxidase, cholesterol oxidase and galactose oxidase.

As an illustrative example, a composition suitable for use as an anti-toxin formulation may comprise from about 10 to 5,000 µg/ml of myeloperoxidase, from 0.3 to 50 mM of glycine, from 0.3 to 50 mM of l-alanine, from 0.3 to 50 mM of l-proline, and from 1 to 500 units/ml of glucose oxidase.

The compositions of the present disclosure may also comprise halide. When the halide is chloride, the amount of chloride used in the compositions of the present disclosure will preferably fall in the range of about 10 µmol chloride to about 200 µmol per ml of solution (i.e., 10 to 200 mEq chloride/L) chloride. The physiologic concentration of chloride in plasma is about 105 mEq/L. When included, the compositions of the present disclosure may comprise from about 0.5 µmol bromide to about 20 µmol bromide per ml (i.e., 0.5 to 20 mEq bromide/L) of liquid composition, more preferably from about 1 µmol bromide to about 10 82 mol bromide per ml (i.e., 1 to 10 mEq bromide/L) of liquid composition, and most preferably from about 100 nmol bromide to about 1 µmol bromide per ml of liquid composition.

The compositions may additionally comprise a pharmaceutically acceptable carrier. In some embodiments, the compositions may be conveniently provided in a liquid carrier. Any liquid carrier may be generally used for this purpose, provided that the carrier does not significantly interfere with the selective binding capabilities of the myeloperoxidase or with enzyme activity (if microbicidal action is desired). Alternatively, the compositions may be provided in solid form with activation on solubilization in liquid.

In embodiments that include a substrate for the peroxide-producing oxidase, the myeloperoxidase/oxidase system lends itself to construction as a binary formulation in which the composition's active agents are formulated in two separate parts for consolidation at the time of use. For example, the first composition of the binary formulation may comprise a solution containing the myeloperoxidase and the oxidase. In some embodiments, the first composition comprises two or three amino acids. In some embodiments, the three amino acids are glycine, l-alanine and l-proline. The second composition of the binary formulation may comprise a substrate for the oxidase, e.g., glucose (i.e., dextrose) in the case of glucose oxidase. The substrate may be provided, for example, in the form of a solid wafer. In some embodiments, the myeloperoxidase composition may additionally comprise alcohol in order to facilitate oxidase substrate solubilization and utilization by the oxidase.

In one embodiment, the methods of the present disclosure comprise administering to the site of infection a first composition comprising myeloperoxidase, a peroxide-producing oxidase and at least two amino acids; and administering to the site of infection a second composition comprising a substrate for the oxidase. In some embodiments the first composition and the second composition are mixed before administration to the site of infection. In some embodiments the first composition and the second composition are administered concurrently to the site of infection. In some embodiments the first composition and the second composition are administered sequentially to the site of infection. The first composition and the second composition may be administered in any order.

The binary formulation described above may be used to exert microbicidal action and may be used to increase the inhibition of endotoxin, but is not required for inhibition of lipopolysaccharide and lipid A by myeloperoxidase or a myeloperoxidase-oxidase complex.

For topical applications, the detoxifying compositions can be administered in any effective pharmaceutically acceptable form to warm blooded animals, including human and animal subjects, e.g., in topical, lavage, oral, vaginal or rectal suppository dosage forms, as a topical, buccal, nasal spray, aerosol for inhalation or in any other manner effective to deliver active myeloperoxidase to a site of bacterial infection. The route of administration will preferably be designed to obtain direct contact of the compositions with the toxins produced by or associated with the infecting bacteria. In one aspect of the present disclosure, the compositions of the present disclosure are delivered or administered topically to areas of a human or animal subject that are infected or susceptible to infection, such as, for example, to the gums, eyes, ears, skin, wounds, vaginal areas, groin areas, bed sores, burns, areas under medical dressings, diapers or other coverings which are likely to be moist, and the like.

For topical applications, the pharmaceutically acceptable carrier may take the form of liquids, creams, foams, lotions, ointments, suspensions, suppositories or gels, and may additionally comprise aqueous or organic solvents, buffering agents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration. In addition, the compositions of the present disclosure may be impregnated in dressings or coverings for application to a subject.

The foregoing may be better understood in connection with the following representative examples, which are presented for purposes of illustration and not by way of limitation.

EXAMPLES

The inhibition of bacterial endotoxin lipopolysaccharides and lipid A by various agents was studied using the Limulus Amebocyte Lysate Endosafe® Endochrome-K™ kit ("LAL") available from Charles River Endosafe, Charleston, S.C. The LAL assay is a means to detect and measure bacterial endotoxin activity in a sample. The LAL assay used in the following examples is a kinetic colorimetric assay that detects and measures the onset of color. The time of onset of color is inversely related to the amount of endotoxin in a sample. Endotoxin levels in an unknown sample are determined by comparison to a standard curve. The amount of endotoxin present in a sample is designated by endotoxin units ("EU"). The Endosafe® LAL assay can detect from 100-0.001 EU/ml.

Example 1

This example demonstrates the inhibition of lipopolysaccharide endotoxin by compositions comprising myeloperoxidase. The following four agents, or combinations of agents, were tested: (1) myeloperoxidase; (2) glucose oxidase; (3) myeloperoxidase, glucose oxidase and amino acids; and (4) myeloperoxidase, glucose oxidase, glucose, and amino acids.

The myeloperoxidase ("MPO") used in this example was porcine myeloperoxidase (Exoxemis, Inc., Little Rock, Ark. U.S.A.). The glucose oxidase ("GO") was from Aspergillus niger and was purchased from Biozyme, Inc., UK. The myeloperoxidase and glucose oxidase were further purified by passing the MPO or GO through a polymyxin b column twice to remove LPS present in the test additives using the Toxin Eraser Endotoxin Removal Kit available from Genscript, cat #L00338.

Procedure. Stock solutions were made of the following test additives: myeloperoxidase (1 mg/ml); glucose oxidase (1 mg/ml); E-101 (enzyme) (1 mg/ml MPO; 0.25 mg/ml GO); E-101 (substrate) (27 mg/ml glucose final); E-101 (complete) (1 mg/ml MPO; 0.25 mg/ml GO; 54 mg/ml glucose).

As used herein, the term "E-101 (enzyme)" refers to a solution comprised of myeloperoxidase, glucose oxidase and amino acids glycine, alanine, and proline in an aqueous vehicle comprising 150 mM sodium chloride and 0.02% w/v polysorbate 80 in 20 mM sodium phosphate buffer pH 6.5.

As used herein, the term "E-101 (substrate)" refers to a solution of 27 mg/ml glucose in an aqueous vehicle comprising 150 mM sodium chloride and 0.02% w/v polysorbate 80 in 20 mM sodium phosphate buffer pH 6.5.

As used here, the term "E-101 (complete)" refers to a formulation formed by combining one part E-101 (enzyme) and two parts E-101 (substrate).

Testing was performed on 96-well microtiter plates using a final volume of 100 µL per well. Reagents were prepared at twice the final desired concentration, and 50 µL volumes were added per well. 50 µL of LPS endotoxin was added per well. In wells where a reagent was omitted, its volume was replaced with an equal volume of low endotoxin reagent water ("LRW") supplied with the Endosafe® assay kit.

The ability of myeloperoxidase compositions to inhibit lipopolysaccharide was determined by measuring endotoxin inhibition at increasing amounts of endotoxin and decreasing amounts of myeloperoxidase in the test solutions, i.e., over a range of endotoxin:myeloperoxidase ratios. This approach allowed estimation of maximum inhibitory activity of one milligram of myeloperoxidase where endotoxin availability was limiting, and also enabled the comparison of inhibitory activity of myeloperoxidase to glucose oxidase and in combination with glucose oxidase, with and without substrate.

Eight activities (concentrations) of LPS were tested: 40 EU, 80 EU, 120 EU, 300 EU, 600 EU, 10000 EU, 20000 EU, and 40000 EU per test solution. The concentration of myeloperoxidase varied from 1 mg/ml to 0.03 mg/ml test solution. The concentration of glucose oxidase when tested alone varied from 1 mg/ml to 0.03 mg/ml. The concentration of glucose oxidase tested in combination with myeloperoxidase varied from 0.25 mg/ml to 0.0075 mg/ml. (The ratio of MPO to GO in E101 enzyme and E101 complete was 4:1.) Serial dilutions were made using the low endotoxin reagent water (LRW) supplied with the Endosafe® assay kit.

Lipopolysaccharide was pre-incubated with the various test additives for 30 minutes before the LAL assay was run to determine the amount of endotoxin activity present in the test samples. After the pre-incubation period, 100 µL of chromogenic Limulus Amebocyte Lysate (LAL) solution (Charles River Kit R1708K) was added and the change in absorbance was measured using a Tecan Sunrise microplate spectrophotometer at a wavelength of 405 nm. The amount of endotoxin inhibited at the various concentrations of test agents was determined and then the value was extrapolated to determine the number of endotoxin units inhibited per milligram of myeloperoxidase. For example, if a sample containing 40 EU LPS and 0.5 mg/ml of MPO resulted in complete inhibition of the 40 EU, then the number of EU inhibited by 1 mg of MPO was calculated to be 80 EU.

The results are shown in Table 1 below. The data in Table 1 reports the amount of endotoxin units inhibited by 1 mg MPO.

TABLE 1

Lipopolysaccharide Endotoxin Units Inhibited/mg MPO

| EU Initial Concentration | MPO | GO | E101 (Enzymes) | E101 (Complete) |
|---|---|---|---|---|
| 40 EU | 140* EU | 70** EU | 320*** EU | 528*** EU |
| 80 EU | 154 EU | 79 EU | 640 EU | 640 EU |
| 120 EU | 113 EU | 115 EU | 960 EU | 944 EU |
| 300 EU | 3600 EU | 291 EU | 2400 EU | 2400 EU |
| 600 EU | 4256 EU | 532 EU | 4800 EU | 4472 EU |
| 1000 EU | 5096 EU | 3056 EU | 8000 EU | 6696 EU |
| 2000 EU | 6984 EU | 6984 EU | 15816 EU | 11056 EU |
| 4000 EU | 13360 EU | 13360 EU | 15672 EU | 26720 EU |

*35 of 40 EU inhibited by 0.25 mg/ml MPO extrapolates to 140 EU inhibited per 1 mg MPO
**35 of 40 EU inhibited by 0.5 mg/ml GO extrapolates to 70 EU inhibited per 1 mg GO
***E101 (enzymes) and E101 (complete) comprise MPO and GO in a ratio of 4:1. Inhibitory activity is calculated per mg of MPO.

The above data illustrate that myeloperoxidase is a potent inhibitor of lipopolysaccharide endotoxin. The data illustrate that one milligram of myeloperoxidase can inhibit more than 10,000 EU/mL of LPS. Glucose oxidase exhibits about half the inhibitory effect of myeloperoxidase when LPS is tested at low concentrations, but at higher LPS doses (e.g., 4,000 EU/mL), GO also inhibits greater than 10,000 EU/mL.

In sharp contrast to MPO and GO individually, the combination of one milligram of myeloperoxidase and 0.25 milligrams of glucose oxidase exhibits an inhibitory effect several fold greater than the effect achieved with myeloperoxidase without glucose oxidase. Similar results were found for myeloperoxidase in combination with glucose oxidase and glucose (substrate for the glucose oxidase).

Example 2

This example demonstrates the inhibition of lipid A, the toxic component of lipopolysaccharide, by compositions comprising myeloperoxidase. In this example, the ability of myeloperoxidase compositions to inhibit lipid A was determined by measuring endotoxin inhibition at increasing amounts of lipid A and decreasing amounts of myeloperoxidase in the test solutions, i.e., over a range of endotoxin:myeloperoxidase ratios. The test solutions had the same components and concentrations as in Example 1 and the procedure was the same. Nine activities (concentrations) of lipid A were tested: 10 EU, 20 EU, 40 EU, 80 EU, 300 EU, 600 EU, 1000 EU, 2000 EU, and 4000 EU per test solution. Calculations were performed as in Example 1 to determine the number of lipid A endotoxin units inhibited per milligram of myeloperoxidase. The results are reported in Table 2 below.

TABLE 2

Lipid A Endotoxin Units Inhibited/mg MPO

| EU Initial Concentration | MPO | GO | E101 (Enzymes) | E101 (Complete) |
|---|---|---|---|---|
| 10 EU | 9 EU | <5 EU | 320 EU | 320 EU |
| 20 EU | 30 EU | <5 EU | 640 EU | 640 EU |
| 40 EU | 27 EU | <5 EU | 640 EU | 496 EU |
| 80 EU | 88 EU | <5 EU | 2560 EU | 1504 EU |
| 300 EU | 336 EU | <5 EU | 9568 EU | 7456 EU |
| 600 EU | 534 EU | 124 EU | 18434 EU | 18176 EU |
| 1000 EU | 2616 EU | 200 EU | 27104 EU | 13408 EU |
| 2000 EU | 4028 EU | 823 EU | 55808 EU | 50368 EU |
| 4000 EU | 8328 EU | 591 EU | 92864 EU | 43760 EU |

The data in Table 2 illustrate that the inhibitory effect of myeloperoxidase alone, and myeloperoxidase in combination with glucose oxidase, on lipid A activity is even more dramatic than the data in Table 1 illustrating the inhibitory effect of myeloperoxidase on lipopolysaccharide activity. The data in Table 2 show that glucose oxidase alone has little inhibitory effect on lipid A, but the inhibitory effect of myeloperoxidase alone on lipid A is greater than 8,000 EU per mg MPO (extrapolated from the inhibition of 4,000 EU of lipid A). At the same 4,000 EU lipid A concentration, the combination of MPO and GO exhibits an inhibitory effect on lipid A of greater than 92,000 EU per mg myeloperoxidase.

These data show that glucose oxidase and myeloperoxidase in combination act synergistically as a potent inhibitor of gram-negative bacteria lipid A endotoxin activity. Moreover, as in Example 1, the data show that the endotoxin inhibitory action is independent of haloperoxidase microbicidal activity. It is notable that inhibitory action with regard to lipid A appears to be mildly decreased in the enzymatically active preparation.

Example 3

The data in Tables 1 and 2 illustrate that the myeloperoxidase and myeloperoxidase:glucose oxidase inhibition of endotoxin is proportional to the concentration of endotoxin tested (LPS or lipid A); i.e., the reaction is essentially first order with respect to increasing endotoxin over the range of endotoxin tested.

To test the limit of myeloperoxidase inhibition of endotoxin, high concentrations of LPS and lipid A were tested by using a constant concentration of MPO, E101 enzyme (MPO:GO) or E101 complete (MPO:GO:glucose) equivalent to 1 mg/mL MPO, and varying the concentration of LPS and lipid A by $2^n$ dilutions from 10,000,000 EU/mL (3.3 mg/mL of LPS, and 3.0 mg/mL lipid A) to 312,500 EU/mL. The results are shown in Tables 3 and 4 below.

TABLE 3

Lipopolysaccharide Endotoxin Units Inhibited/mg MPO

| EU Initial Concentration | EU Activity Measured | | | |
|---|---|---|---|---|
| | MPO | GO* | E101 (Enzymes) | E101 (Complete) |
| 10,000,000 EU | decreased but too high to measure | too high to measure | 0 EU | 0 EU |
| 5,000,000 EU | decreased but too high to measure | too high to measure | 0 EU | 0 EU |
| 2,500,000 EU | decreased but too high to measure | too high to measure | 0 EU | 0 EU |
| 1,250,000 EU | decreased but too high to measure | too high to measure | 0 EU | 0 EU |
| 625,000 EU | decreased but too high to measure | too high to measure | 0 EU | 0 EU |
| 312,500 EU | decreased but too high to measure | too high to measure | 0 EU | 0 EU |

*1 mg/ml glucose oxidase

TABLE 4

Lipid A Endotoxin Units Inhibited/mg MPO

| EU Initial Concentration | EU Activity Measured | | | |
|---|---|---|---|---|
| | MPO | GO* | E101 (Enzymes) | E101 (Complete) |
| 10,000,000 EU | too high to measure | too high to measure | 0 EU | 0 EU |
| 5,000,000 EU | too high to measure | too high to measure | 0 EU | 0 EU |
| 2,500,000 EU | too high to measure | too high to measure | 0 EU | 0 EU |
| 1,250,000 EU | too high to measure | too high to measure | 0 EU | 0 EU |
| 625,000 EU | too high to measure | too high to measure | 0 EU | 0 EU |
| 312,500 EU | too high to measure | too high to measure | 0 EU | 0 EU |

The data in Tables 3 and 4 illustrate that at the highest concentration (10,000,000 EU/mL), LPS and lipid A were completely inhibited by 1 mg/mL MPO in combination with GO, i.e. E101 enzyme (MPO:GO), or E101 complete (MPO:GO:glucose), and MPO alone showed partial inhibition (delayed EU kinetic), but could not be further quantified.

These data clearly show myeloperoxidase and glucose oxidase act synergistically to inhibit lipopolysaccharide (endotoxin) and lipid A of gram-negative bacteria. Moreover, because the inhibitory effect of MPO/GO is about the same as the inhibitory effect of MPO/GO plus glucose, the data shows that the endotoxin inhibitory action is independent of haloperoxidase microbicidal activity.

While illustrative embodiments have been illustrated and described, it will be appreciated that various changes can be made therein without departing from the spirit and scope of the present disclosure.

I claim:

1. A method of inhibiting activity of a lipopolysaccharide endotoxin present at a site in a human or animal subject infected with gram negative bacteria, the method consisting of administering a composition to the site where the lipopolysaccharide endotoxin is present, the composition consisting of myeloperoxidase and a pharmaceutically acceptable carrier, wherein the myeloperoxidase directly contacts, binds to, and inhibits the activity of the lipopolysaccharide endotoxin.

2. The method of claim 1, wherein the lipopolysaccharide endotoxin comprises lipid A, and the myeloperoxidase binds to the lipid A to thereby inhibit endotoxin activity of the lipid A.

3. The method of claim 1, wherein the lipopolysaccharide endotoxin is associated with the gram negative bacteria.

4. The method of claim 1, wherein the lipopolysaccharide endotoxin is produced by the gram negative bacteria.

5. The method of claim 1, wherein the myeloperoxidase composition is administered in a pharmaceutically acceptable form to deliver the myeloperoxidase to the site of the lipopolysaccharide endotoxin.

6. The method of claim 5, wherein the pharmaceutically acceptable form is a topical, lavage, oral, vaginal, or rectal suppository form.

* * * * *